United States Patent
Romero et al.

(10) Patent No.: US 7,148,836 B2
(45) Date of Patent: Dec. 12, 2006

(54) OBSTACLE PENETRATING DYNAMIC RADAR IMAGING SYSTEM

(75) Inventors: Carlos E. Romero, Livermore, CA (US); James E. Zumstein, Livermore, CA (US); John T. Chang, Danville, CA (US); Richard R. Leach, Jr., Castro Valley, CA (US)

(73) Assignee: The Regents of the University of California, Oakland, CA (US)

( * ) Notice: Subject to any disclaimer, the term of this patent is extended or adjusted under 35 U.S.C. 154(b) by 15 days.

(21) Appl. No.: 11/069,329

(22) Filed: Feb. 28, 2005

(65) Prior Publication Data
US 2006/0170584 A1 Aug. 3, 2006

Related U.S. Application Data

(60) Provisional application No. 60/550,783, filed on Mar. 5, 2004.

(51) Int. Cl.
*G01S 13/89* (2006.01)
*G01S 13/88* (2006.01)

(52) U.S. Cl. ............ 342/22; 342/27; 342/179
(58) Field of Classification Search ......... 342/22, 342/27, 179
See application file for complete search history.

(56) References Cited

U.S. PATENT DOCUMENTS

| 5,111,695 A | 5/1992 | Engeler et al. |
| 5,381,151 A * | 1/1995 | Boles et al. ............ 342/21 |
| 5,446,461 A * | 8/1995 | Frazier ............... 342/22 |
| 5,465,094 A | 11/1995 | McEwan |
| 5,512,834 A | 4/1996 | McEwan |
| 5,573,012 A | 11/1996 | McEwan |

(Continued)

FOREIGN PATENT DOCUMENTS

EP 0 799 428 B1 2/2002

(Continued)

OTHER PUBLICATIONS

Withington et al., "Enhancing Homeland Security with Advanced UWB sensors," IEEE Microwave magazine, Sep. 2003.*

(Continued)

*Primary Examiner*—Ian J. Lobo
(74) *Attorney, Agent, or Firm*—Eddie E. Scott; Alan H. Thompson

(57) ABSTRACT

An obstacle penetrating dynamic radar imaging system for the detection, tracking, and imaging of an individual, animal, or object comprising a multiplicity of low power ultra wideband radar units that produce a set of return radar signals from the individual, animal, or object, and a processing system for said set of return radar signals for detection, tracking, and imaging of the individual, animal, or object. The system provides a radar video system for detecting and tracking an individual, animal, or object by producing a set of return radar signals from the individual, animal, or object with a multiplicity of low power ultra wideband radar units, and processing said set of return radar signals for detecting and tracking of the individual, animal, or object.

21 Claims, 6 Drawing Sheets

U.S. PATENT DOCUMENTS

| | | |
|---|---|---|
| 5,581,517 A | 12/1996 | Gee et al. |
| 5,835,054 A | 11/1998 | Warhus et al. |
| 5,899,861 A | 5/1999 | Friemel et al. |
| 5,900,833 A * | 5/1999 | Sunlin et al. .................. 342/22 |
| 6,218,979 B1 * | 4/2001 | Barnes et al. .................. 342/22 |
| 6,452,988 B1 | 9/2002 | Hayward |
| 6,466,155 B1 * | 10/2002 | Taylor et al. .................. 342/22 |
| 6,598,014 B1 | 7/2003 | Rabideau |
| 6,624,783 B1 | 9/2003 | Rabideau |
| 6,919,838 B1 * | 7/2005 | Santhoff ...................... 342/22 |
| 2002/0175849 A1 * | 11/2002 | Arndt et al. .................. 342/22 |
| 2002/0190915 A1 | 12/2002 | Barnes et al. |
| 2004/0068744 A1 * | 4/2004 | Claussen et al. .............. 725/81 |

FOREIGN PATENT DOCUMENTS

| | | |
|---|---|---|
| WO | WO 00/41162 | 7/2000 |

OTHER PUBLICATIONS

Nag, S., et al., "An Ultra-Wideband Through-Wall Radar for Detecting the Motion of People in Real Time", Radar Sensor Technology and Data Visualizaiton, Proceedings of SPIE vol. 4744, 2002, pp. 48-57.

* cited by examiner

OBSTACLE PENETRATING DYNAMIC RADAR IMAGING SYSTEM

CROSS-REFERENCE TO RELATED APPLICATIONS

This application claims the benefit of U.S. Provisional Patent Application No. 60/550,783 filed Mar. 5, 2004 and titled "Fast Framing, Through Obstacle, Electronically Steerable, Dynamic Radar Imaging Array." U.S. Provisional Patent Application No. 60/550,783 filed Mar. 5, 2004 is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to detection, tracking, and imaging and more particularly to an obstacle penetrating dynamic radar imaging system.

2. State of Technology

United Kingdom Patent Application No. GB2383214 by David Brown, published Jun. 18, 2003, provides the following state of technology information: "In order to determine the location of a person within a building or facility, a number of radio frequency transceivers are positioned at fixed locations throughout the facility and each person is provided with a portable radio frequency transceiver. Each of the fixed transceivers is operable to communicate the identity of one or more portable transceivers located within communications range of a fixed transceiver to a central processing unit. The coverage area provided by the transceivers within a facility may be remotely or automatically adjusted. The location of an individual may be determined by a triangulation process. The fixed position transceivers may be arranged in cells comprising a number of pico-net masters and further scatter-net masters arranged to relay information to a central processing unit. The transceivers may be operated in accordance with the Bluetooth RTM communications protocol. The system may be arranged to track movements of individuals via the use of a video-surveillance system; remotely control the operation of a device within the vicinity of an individual; monitor the locations of a number of people within an airport; monitor the location of an isolated worker whereby in the event of an provided to the central processing unit via a fixed transceiver."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides an obstacle penetrating dynamic radar imaging system for the detection, tracking, and imaging of an individual, animal, or object. The system comprises a multiplicity of low power ultra wideband radar units that produce a set of return radar signals from the individual, animal, or object, and a processing system for said set of return radar signals for detection, tracking, and imaging of the individual, animal, or object. The system provides a radar video system for detecting and tracking an individual, animal, or object by producing a set of return radar signals from the individual, animal, or object with a multiplicity of low power ultra wideband radar units, and processing said set of return radar signals for detecting and tracking of the individual, animal, or object.

The obstacle penetrating dynamic radar imaging system of the present invention has the capability of being lightweight and portable, but can also be used in any of a multitude of other applications, including built-in systems for infrastructure applications, heavier systems for long-life and longer-range applications. Resolution for any given embodiment can be realized by changing aperture size and/or system frequency. Target identification is not limited to moving objects, but extend to any object that has the ability to reflect the radiated energy, whether that object is, has been, or is not in motion. Target identification is not limited to one object. Any number of objects may be identified within the field of view of the radiated energy. Interpretation of received energy can be done with automated processing algorithms and/or using the human expert to determine target characterization.

The obstacle penetrating dynamic radar imaging system of the present invention allows monitoring of military and criminal situations in buildings and behind other obstructions. The obstacle penetrating dynamic radar imaging system of the present invention allows military, rescue forces, police, or other forces to detect the presence and location of individuals hidden by obstacles such as smoke, haze, walls, rubble, or other obstructions. The obstacle penetrating dynamic radar imaging system will allow military and other forces to detect and locate enemy soldiers or terrorists through obscurants such as buildings, smoke, mist, and fog. The obstacle penetrating dynamic radar imaging system will allow rescue forces to detect and locate survivors buried in rubble nearby, and at extended distances. The obstacle penetrating dynamic radar imaging system can be used by firefighters to monitor and keep track of individual firefighters in burning buildings through obscurants such as smoke, mist, and fog. Other uses include, but are not limited to, the following: concealed threat detection, hostage situations, facility protection, military and police action, search and rescue, prisoner monitoring, non-destructive evaluation, troop and soldier monitoring, prisoner monitoring, bridge inspection, medical imaging, medical diagnostics, and medical treatment.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
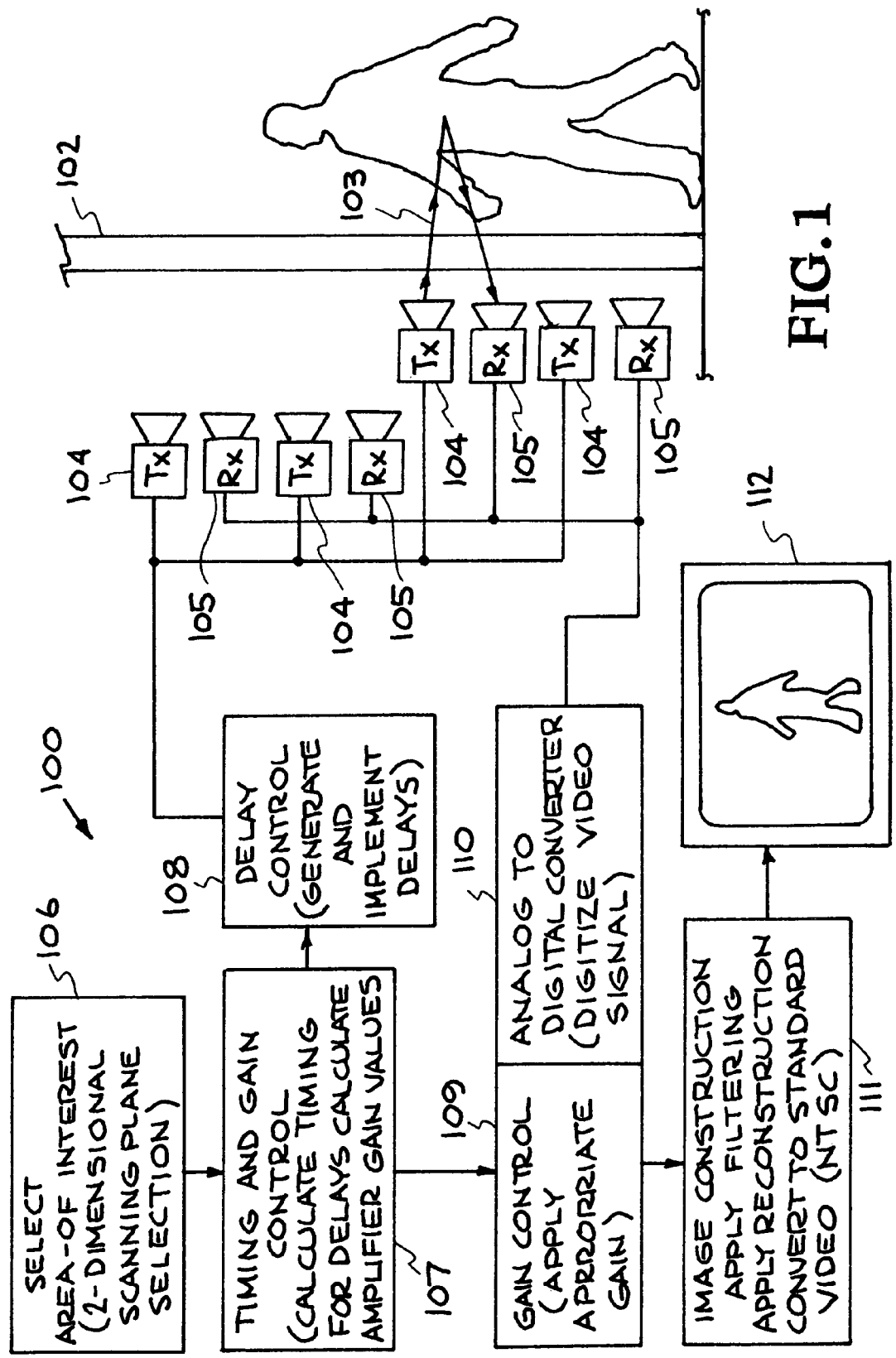
FIG. 1 is a block diagram illustrating one embodiment of an obstacle penetrating dynamic radar imaging system incorporating the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to the drawings and in particular to FIG. 1, a block diagram illustrating one embodiment of a obstacle penetrating dynamic radar imaging system incorporating the present invention is shown. The obstacle penetrating dynamic radar imaging system of this embodiment is designated generally by the reference numeral 100. The target the radar is illuminating is designated generally by the reference numeral 101. The target 101 the radar is illuminating in this instance is a person such as a terrorist or a criminal. The obstacle that is penetrated by the radar is designated generally by the reference numeral 102. The obstacle 102 that is penetrated by the radar is a wall such as the wall of a building. The electromagnetic radar signal is designated generally by the reference numeral 103. The electromagnetic radar signal 103 is an electro-magnetic radar signal emanating from any transmitter in the system, traveling through space, barriers, etc., reflecting off of a target, and finally being recovered at any or all of the radar receivers. The obstacle penetrating dynamic radar imaging system 100 includes the following structural components: radar transmitter and antenna 104, radar receive and antenna 105, touch-screen for selection of area-of-interest 106, timing and gain control circuitry 107, delay control circuitry 108, gain control circuitry 109, transmitter delay control board 107, analog to digital converter and amplifier gain board 110, image construction board 111, and video display monitor 112.

Radar imaging has been used for the identification of objects. An electromagnetic pulse, or wave is sent emitted through free-space and/or materials, walls, etc. The reflected energy is then captured and an ensemble image of radar returns is created. From these images, it is then possible to locate and potentially identify objects, for example aircraft in flight, rebar under concrete, or humans behind walls. Typically the use of synthetic aperture radar (SAR) has been applied to achieve this. SAR techniques have several limitations, such as they require slow, bulky mechanical systems to position and fire the radar and poor signal to noise ratio (SNR). Additionally, the ability to discriminate hidden objects is limited and typical time consuming (minutes to hours) post processing of the collected data limits the utility of this approach. A critical limitation of using SAR and inverted SAR (ISAR) systems is their requirement that the targets of interest or the radar system itself be in motion relative to each other.

The obstacle penetrating dynamic radar imaging system 100 combines several ideas to form a device, which overcomes these limitations and allows simultaneous identification of a multitude of objects, hidden and otherwise. It is small, portable, fast, has a high SNR, and has the ability to generate real time radar images at rates of up to 30 frames per second and higher. The obstacle penetrating dynamic radar imaging system 100 improves the low SNR by the use of delay and sum beam formers and permits multiple radar elements to focus their energies at the same point in space and time. This juxtaposition of waveforms then increases the SNR by $N^3$ where N is the number of radar focusing elements. A distinct advantage of our approach is that, while the system is lightweight and portable, it also allows imaging of stationary objects while the system is also stationary. This is critical for identification of non-moving targets and objects of interest.

Incorporating motion in the generation of dynamic radar images is important and useful in the interpretation of what physical objects the radar images represent. The obstacle penetrating dynamic radar imaging system 100 has been developed which uses a steerable array of microwave radars that enables up to 3 dimensional (3D) imaging of hidden objects. The array control board calculates the delays required to beam form on transmit and receive and controls an array of transmit/received channels (reduced to practice 32 transmit/receive channels). The delay board implements the necessary delays for a multitude of transmit/receive channels (reduced to 4 transmit/receive channels). Compensation for attenuation through space and variable receiver gain is achieved through a programmable gain board, which supports a multitude of channels/board (reduced to practice 4 channels/board). The system is capable of sampling any volume in space. (Reduced to practice 5e6 points per second. This translates to a rate of 16 frames per second at a frame size of 640×480, or 30 frames per second at a frame size of 460×354). Auto focusing algorithms, along with multiple signal and image processing algorithms, are performed either on an onboard, embedded DSP processor, FPGA/CPLD chip, notebook/desktop computer or a similar device. Resolution of the hidden objects depends on the bandwidth of the array elements and the aperture of the array. Typical settings provides less than 1 cm resolution in the range (radial distance) direction and less than 10 cm resolution in the transverse (angular) direction.

The structural components of the obstacle penetrating dynamic radar imaging system 100 having been described and illustrated in FIG. 1, the construction and operation of the obstacle penetrating dynamic radar imaging system 100 will now be described. The system 100 utilizes sensors 104 and 105 to provide a real-time view of motion behind an obstruction 102. Radar sensors 104 and 105 in the system 100 producing real-time video (30 frames per second), which shows much greater detail than previous systems. The radar sensors 104 produce electromagnetic radar signals emanating from any of the transmitters in the system 100, travel through space, barrier 102, etc., reflecting off of the target 101, and finally being recovered at any or all of the radar receivers 105.

The special beam-forming hardware and signal processing provides real-time images of an individual 101 through the obstruction 102. The special beam-forming hardware and signal processing of touch-screen for selection of area-of-interest 106, timing and gain control circuitry 107, delay control circuitry 108, gain control circuitry 109, transmitter delay control board 107, analog to digital converter and amplifier gain board 110, image construction board 111, and video display monitor 112 calculates both the time delays and the gains necessary to scan an arbitrary set of points in space. This information is loaded onto the array control boards, which tell the delay boards when to implement the necessary delays and programmable gain boards when to implement the necessary gains. Once the delay boards get their command, they delay the firing of their corresponding transmitters 104 and receivers 105 such that beam 103 forming is achieved both on transmit and receive. Once the programmable gain boards get their command, they apply the appropriate gain to the received signals so that compensation for attenuation through space can be taken into account. Finally, these signals are taken back into the display monitor 112 to be displayed.

The obstacle penetrating dynamic radar imaging system 100 will allow military, rescue forces, police, or other forces to detect the presence and location of individuals hidden by obstacles such as smoke, haze, walls, rubble, or other obstructions. The obstacle penetrating dynamic radar imaging system will allow military and other forces to detect and locate enemy soldiers or terrorists through obscurants such as buildings, smoke, mist, and fog. The obstacle penetrating dynamic radar imaging system will allow rescue forces to detect and locate survivors buried in rubble at extended distances. The obstacle penetrating dynamic radar imaging system can be used by firefighters to monitor and keep track of individual firefighters in burning buildings through obscurants such as smoke, mist, and fog.

Figure 2:
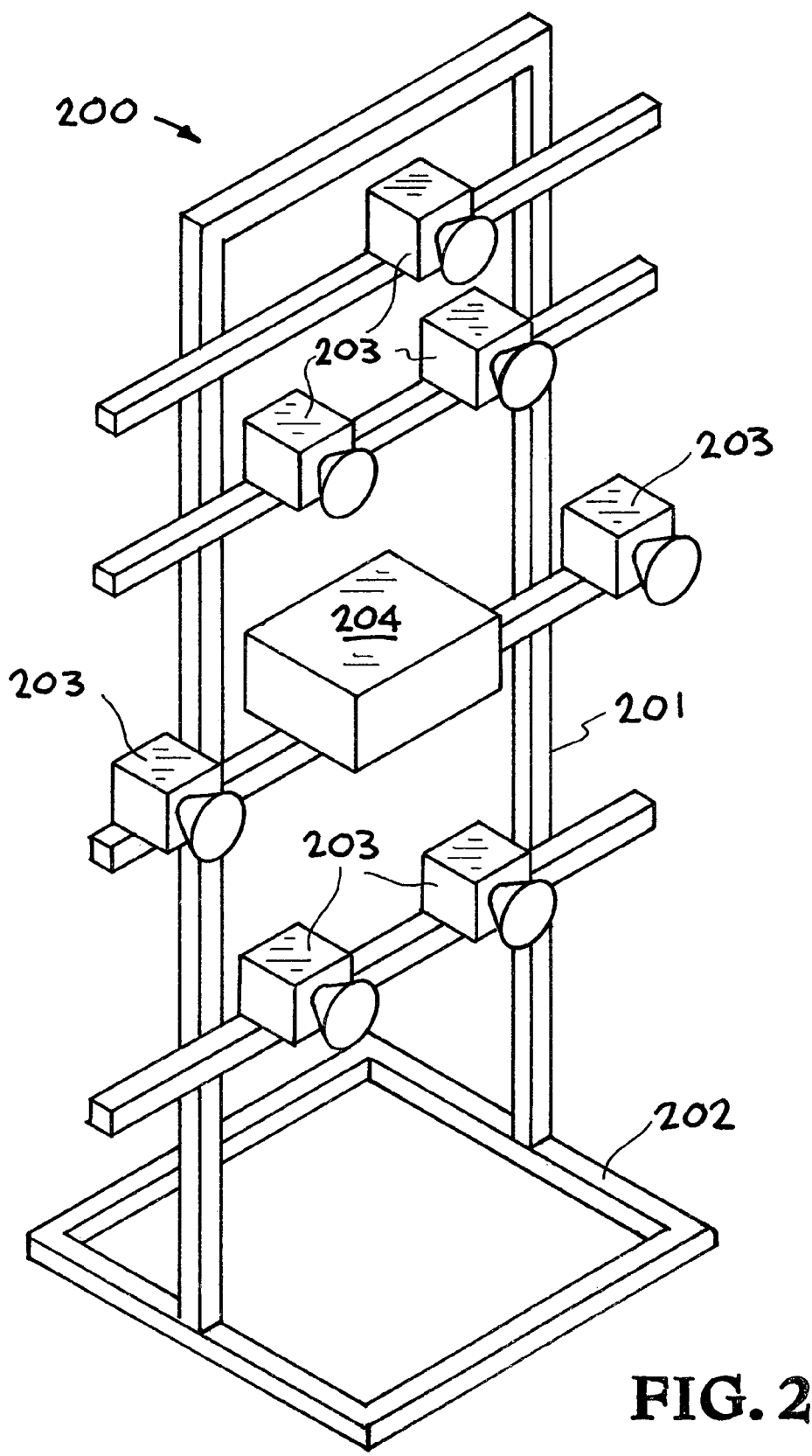
FIG. 2 shows radar array configuration and mount of one embodiment of an obstacle penetrating dynamic radar imaging system incorporating the present invention.

Referring now to FIG. 2, a radar array configuration and mount of one embodiment of an obstacle penetrating dynamic radar imaging system incorporating the present invention is shown. The radar array configuration and mount is designated generally by the reference numeral 200. A frame 201 is mounted on a base 202. The frame 201 mounts radar units 203 and a computational unit 204 that communicates with a local or remote display device.

The first radar units 203 provide sweeping radar beams that provide an estimate of range to target. They are small, low power ultra wideband radar units. The radar units can have the following features: dual channel radar; low-power; modular design; standardized (USB) interface; swept-range gating radar sensors; center frequency 2.4 GHz; bandwidth ~3 GHz; pulse repetition rate 4 MHz; pulse length ~12 ns; duty cycle ~20%; tuned antenna; high speed data transmitted from UWB radars to remote laptop or PDA; system frame rate dependant on link data rate up to 1 Mbit/second; UWB radars sensitive to high-power radio frequency interference near their center frequency of ~1.9 GHz; data link is robust and capable of non-line-of-sight (LOS) communications over a distance of several hundred feet; and wireless communications.

The system 200 utilizes the radar sensors 203 to provide a real-time view of motion behind an obstruction. They producing real-time video (30 frames per second), which shows much greater detail than previous systems. The radar sensors 203 produce electromagnetic radar signals emanating from any of the transmitters in the system, travel through space, barriers, etc., reflecting off of the target, and finally being recovered at any or all of the radar receivers 203.

Figure 3:
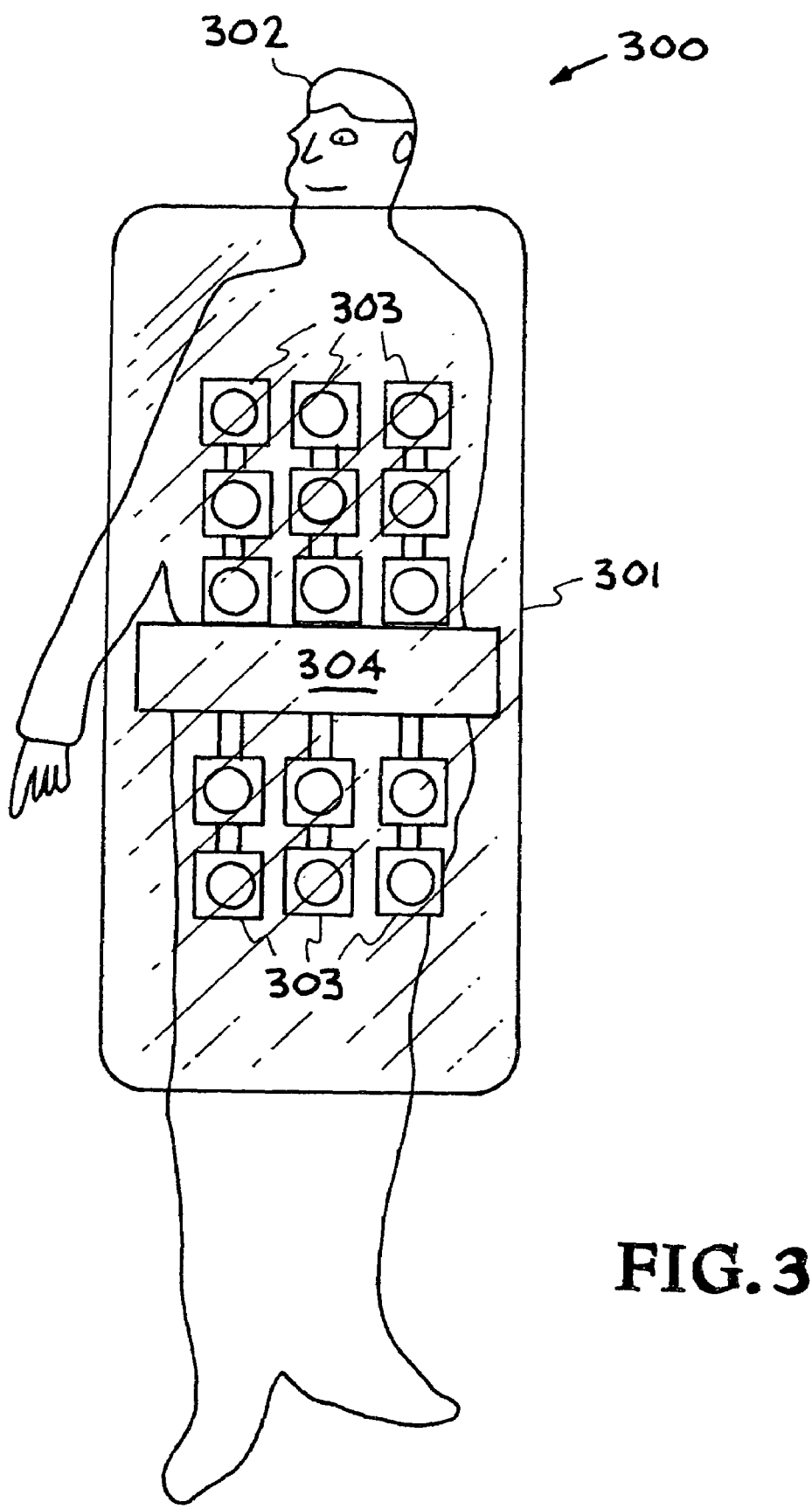
FIG. 3 shows a radar array configuration and mount of another embodiment of an obstacle penetrating dynamic radar imaging system incorporating the present invention.

Referring now to FIG. 3, a radar array configuration and mount of another embodiment of an obstacle penetrating dynamic radar imaging system incorporating the present invention is shown. The radar array configuration and mount is designated generally by the reference numeral 300. A shield 301 is carried by an office 302. The shield 301 mounts radar units 303 and a computational unit 304 that communicates with a remote or local display device.

The radar units 303 provide sweeping radar beams that provide an estimate of range to target. They are small, low power ultra wideband radar units. The system 300 utilizes the radar sensors 303 to provide a real-time view of motion behind an obstruction. They produce real-time video (30 frames per second), which shows much greater detail than previous systems. The radar sensors 303 produce electromagnetic radar signals emanating from any of the transmitters in the system, travel through space, barriers, etc., reflecting off of the target, and finally being recovered at any or all of the radar receivers 303.

Radar imaging has been used to attempt the identification of objects. An electromagnetic pulse, or wave is sent emitted through free-space and/or materials, walls, etc. The reflected energy is then captured and an ensemble image of radar returns is created. From these images, it is then possible to locate and potentially identify objects, for example aircraft in flight, rebar under concrete, or humans behind walls. Typically the use of synthetic aperture radar (SAR) has been applied to achieve this. SAR techniques have several limitations, such as they require slow, bulky mechanical systems to position and fire the radar and poor signal to noise ratio (SNR). Additionally, the ability to discriminate hidden objects is limited and typical time consuming (minutes to hours) post processing of the collected data limits the utility of this approach. A critical limitation of using SAR and inverted SAR (ISAR) systems is their requirement that the targets of interest or the radar system itself be in motion relative to each other.

The present invention as illustrated by the systems 100, 200, and 300, combines several ideas to form a system, which overcomes these limitations and allows simultaneous identification of a multitude of objects, hidden and otherwise. It is small, portable, fast, has a high SNR, and has the ability to generate real time radar images at rates of up to 30 frames per second and higher. The present invention improves the low SNR by the use of delay and sum beam formers and permits multiple radar elements to focus their energies at the same point in space and time. This juxtaposition of waveforms then increases the SNR by $N^3$ where N is the number of radar focusing elements. A distinct advantage of our approach is that, while the system is lightweight and portable, it also allows imaging of stationary objects while the system is also stationary. This is critical for identification of non-moving targets and objects of interest.

The present invention uses a steerable array of microwave radars that enables up to 3 dimensional (3D) imaging of hidden objects. An array control board calculates the delays required to beam form on transmit and receive and controls an array of transmit/received channels (reduced to practice 32 transmit/receive channels). A delay board implements the necessary delays for a multitude of transmit/receive channels (reduced to 4 transmit/receive channels). Compensation for attenuation through space and variable receiver gain is achieved through a programmable gain board, which supports a multitude of channels/board (reduced to practice 4 channels/board). The system is capable of sampling any volume in space. (Reduced to practice 5e6 points per second. This translates to a rate of 16 frames per second at a frame size of 640×480, or 30 frames per second at a frame size of 460×354). Auto focusing algorithms, along with multiple signal and image processing algorithms, are performed either on an onboard, embedded DSP processor, FPGA/CPLD chip, notebook/desktop computer or a similar device. Resolution of the hidden objects depends on the bandwidth of the array elements and the aperture of the array. Typical settings provides less than 1 cm resolution in the range (radial distance) direction and less than 10 cm resolution in the transverse (angular) direction.

Figure 4A:
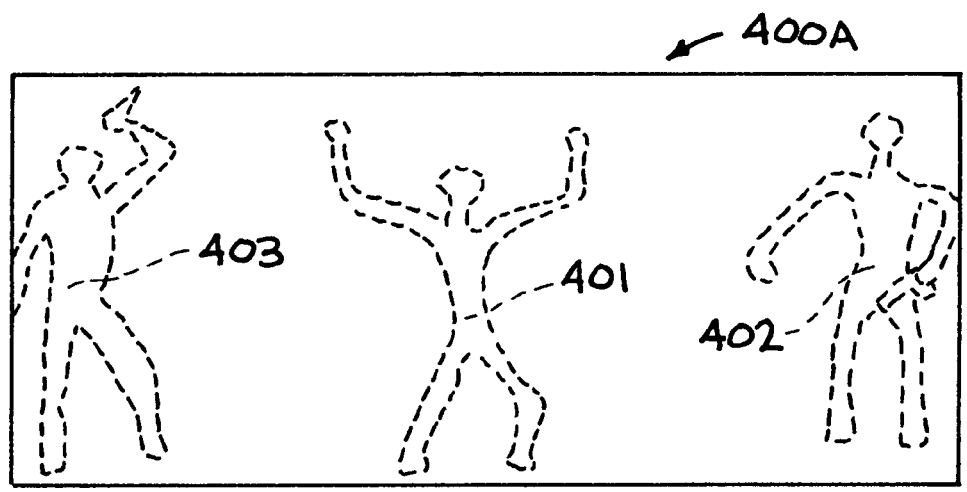
FIG. 4A, FIG. 4B, and FIG. 4C illustrate another embodiment of the obstacle penetrating dynamic radar imaging system of the present invention.
Figure 4B:
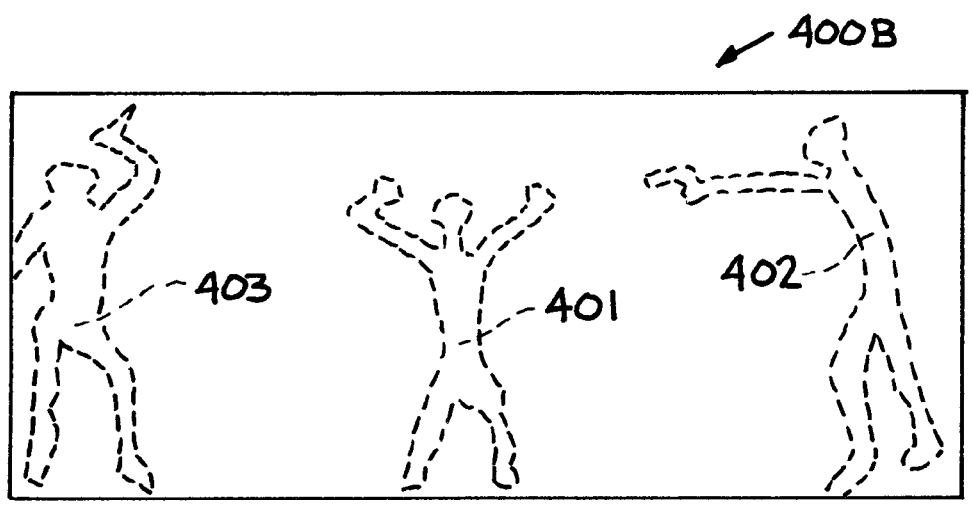
Figure 4C:
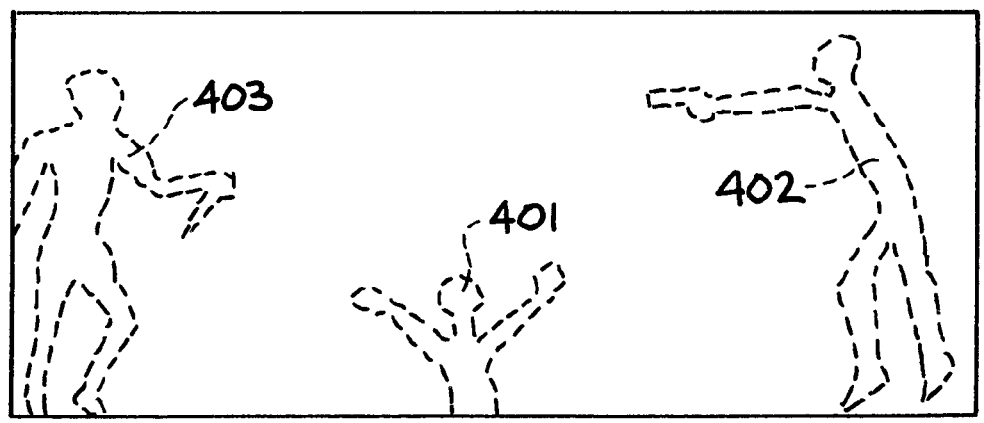

Referring now to FIGS. 4A, 4B, and 4C another embodiment of the obstacle penetrating dynamic radar imaging system of the present invention is illustrated. In this embodiment, three frames from a radar video are shown. The three frames are designated generally by the reference numerals 400A, 400B, and 400C. In the frames 400A, 400B, and 400C, two individuals 402 and 403 are acting out an attack on a third individual 401.

The radar video that produced the three frames 400A, 400B, and 400C was produced with radar sensors producing real-time video (30 frames per second), that shows much greater detail than previous systems. The radar sensors produce electromagnetic radar signals emanating from transmitters in the system. The electromagnetic radar signals travel through space, any intervening barriers and reflect off of the target individuals 401, 402, and 403, and are recovered at radar receivers. Special beam-forming hardware and signal processing provides real-time images of the individuals 401, 402, and 403 through obstructions.

The obstacle penetrating dynamic radar imaging system of the present invention allows monitoring of military and criminal situations in buildings and behind other obstructions. The obstacle penetrating dynamic radar imaging system of the present invention allows military, rescue forces, police, or other forces to detect the presence and location of individuals hidden by obstacles such as smoke, haze, walls, rubble, or other obstructions. The obstacle penetrating dynamic radar imaging system will allow military and other forces to detect and locate enemy soldiers or terrorists through obscurants such as buildings, smoke, mist, and fog. The obstacle penetrating dynamic radar imaging system will allow rescue forces to detect and locate survivors buried in rubble at extended distances. The obstacle penetrating dynamic radar imaging system can be used by firefighters to monitor and keep track of individual firefighters in burning buildings through obscurants such as smoke, mist, and fog. Other uses include, but are not limited to, the following: concealed threat detection, hostage situations, facility protection, military and police action, search and rescue, prisoner monitoring, non-destructive evaluation, troop and soldier monitoring, prisoner monitoring, bridge inspection, medical imaging, medical diagnostics, and medical treatment.

Figure 5:
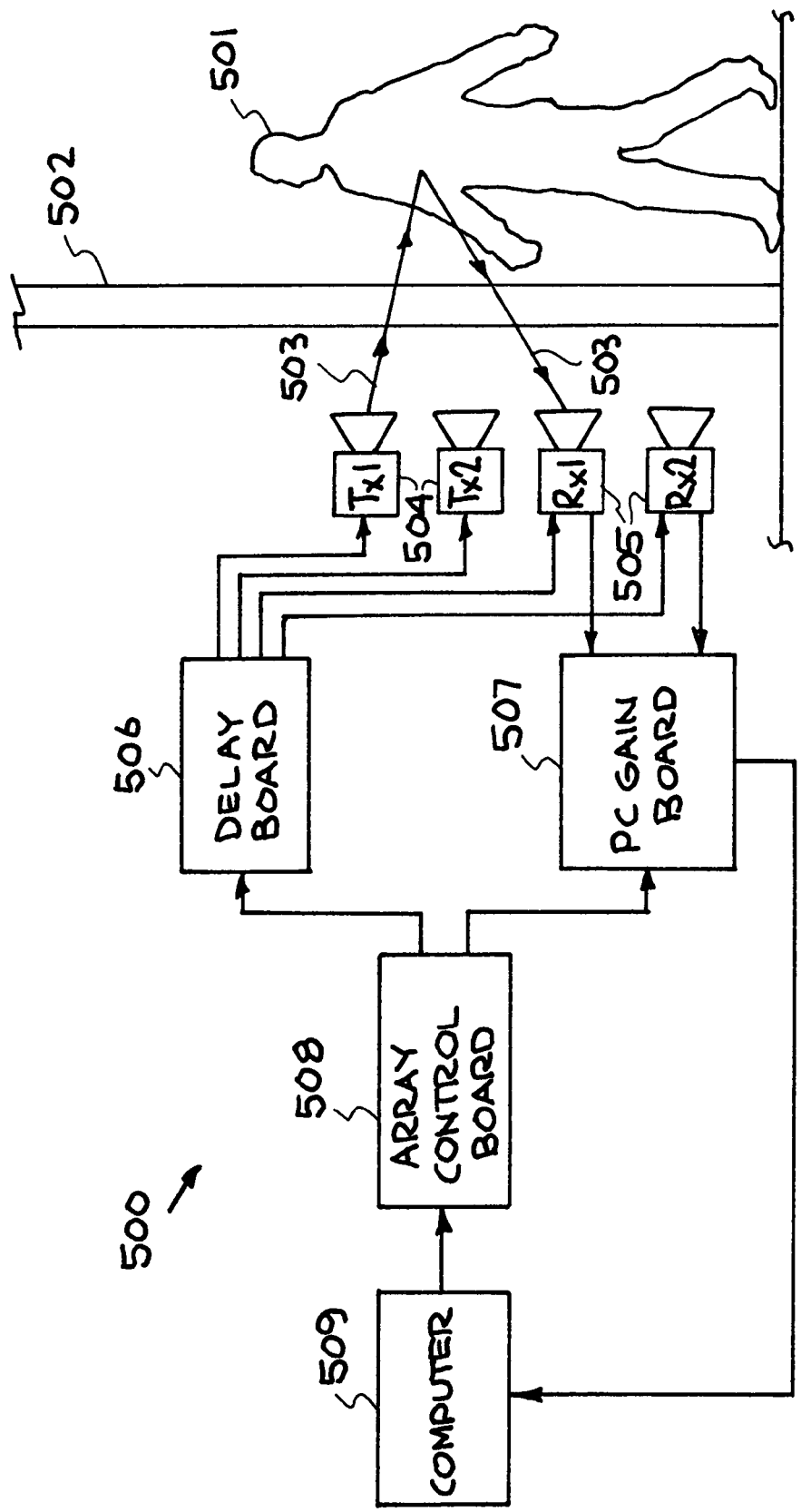
FIG. 5 illustrates another embodiment of obstacle penetrating dynamic radar imaging system incorporating the present invention.

Referring now to FIG. 5, another embodiment of obstacle penetrating dynamic radar imaging system incorporating the present invention is shown. The obstacle penetrating dynamic radar imaging system of this embodiment is designated generally by the reference numeral 500. The target the radar is illuminating is designated generally by the reference numeral 501. The target 501 the radar is illuminating in this instance is a person such as a terrorist or a criminal. The obstacle that is penetrated by the radar is designated generally by the reference numeral 502. The obstacle 502 that is penetrated by the radar is a wall such as the wall of a building. The electromagnetic radar signal is designated generally by the reference numeral 503. The electromagnetic radar signal 503 is an electromagnetic radar signal emanating from any transmitter in the system, traveling through space, barriers, etc., reflecting off of a target, and finally being recovered at any or all of the radar receivers. The obstacle penetrating dynamic radar imaging system 500 includes the following structural components: radar transmitter and antenna 504, radar receiver and antenna 505, delay board 506, PGain board 507, array control board 508, and computer 509.

The array control board 508 controls the firing of the delay boards and the programmable gain boards. Each ACB can control up to 32 channels, where each channel can be either a time delay channel or a gain channel. As many ACBs as necessary can be used to control the elements in the array. In general, one channel is required for each transmitter element (time delay) and two channels for each receiver element (time delay and gain). Technical Specifications for the ACB are as follows:

Size: 3"×4.875"
Power Draw: 0.8 Amps @ 6 Volts
5Controller: 512 va 100 MHz CPLD from Lattice Semiconductor
Memory: 8 M by 16 Non-volatile RAM using DS1265Y/AB from Dallas Semiconductor
Serial Com: RS232 communication @ 115200 baud, 8 bits data, 2 stop bits
Bus: 100 pin board interconnect socket The delay board 506 has four channels, each of which can control the firing of either a transmitter or a receiver. Technical Specifications for the DDB are as follows:

Size: 3"×4.125"
Power Draw: 2 Amps @ 6 Volts
Controller: ispLSI1048EA from Lattice Semiconductor
Channels: 4
Delay Chips/Channel: DS1023-25 and 100E195 ECL from Dallas Semiconductor
Minimum Delay Size: 17.5 ps
Bus: 100 pin board interconnect.

The PGain board 507 has four channels, each of which can apply the corresponding gain to the signal received from a receiver. Hence each PGB can compensate up to 4 receivers. Technical Specifications for the PGB are as follows:

Size: 3"×4.125"
Power Draw: 0.05 Amps @ 6 Volts
Power Converter: +5 Volts to +−12 Volts
Controller: ispLSI1048EA from Lattice Semiconductor
Channels: 4
Gain Chips/Channel: LM6154 quad OpAmps and MAX5436 programmable pots
Gain: 1–100 in steps of 1
Bus: 100 pin board interconnect.

The structural components of the obstacle penetrating dynamic radar imaging system 500 having been described and illustrated in FIG. 5, the construction and operation of the obstacle penetrating dynamic radar imaging system 500 will now be described. The obstacle penetrating dynamic radar imaging system 500 allows for the real time (typically 30 frames/second) radar imaging of both moving and stationary objects through the obstruction 502. The obstruction 502 can be either animate or inanimate. The obstacle penetrating dynamic radar imaging system 500 performs time delay and additive beam forming of a radar antenna array 504 and 505 to rapidly scan multiple times a region in space.

Under such a configuration, the computer 509 calculates both the time delays and the gains necessary to scan an arbitrary set of points in space. This information is loaded onto the Array Control Board 508, which tells delay board 506 when to implement the necessary delays and programmable gain board 507 when to implement the necessary gains. Once the delay board 506 gets its command, it delays the firing of the corresponding transmitters 504 and receivers 505 such that beam forming is achieved both on transmit and receive. Once the programmable gain board 507 gets its command, it applies the appropriate gain to the received signals so that compensation for attenuation through space can be taken into account. Finally, these signals are taken back into the computer 509 to be displayed.

The obstacle penetrating dynamic radar imaging system 500 will allow military, rescue forces, police, or other forces to detect the presence and location of individuals hidden by obstacles such as smoke, haze, walls, rubble, or other obstructions. The obstacle penetrating dynamic radar imaging system will allow military and other forces to detect and locate enemy soldiers or terrorists through obscurants such as buildings, smoke, mist, and fog. The obstacle penetrating dynamic radar imaging system will allow rescue forces to detect and locate survivors buried in rubble at extended distances. The obstacle penetrating dynamic radar imaging system can be used by firefighters to monitor and keep track of individual firefighters in burning buildings through obscurants such as smoke, mist, and fog.

Figure 6:
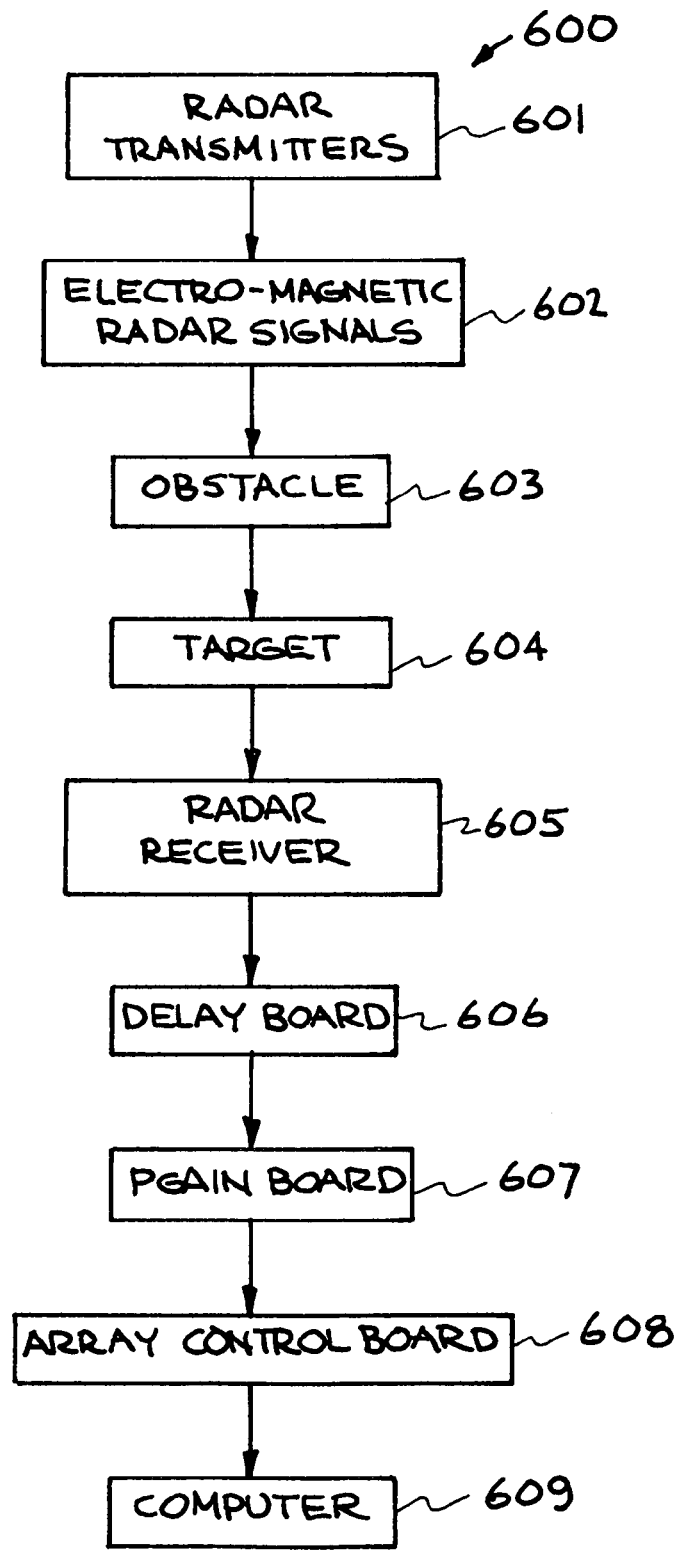
FIG. 6 is a flow diagram that illustrates another embodiment of obstacle penetrating dynamic radar imaging system incorporating the present invention.

Referring now to FIG. 6, a flow diagram illustrates another embodiment of obstacle penetrating dynamic radar imaging system incorporating the present invention. This embodiment of the obstacle penetrating dynamic radar imaging system is designated generally by the reference numeral 600. The obstacle penetrating dynamic radar imaging system 600 allows for the real time (typically 30 frames/second) radar imaging of both moving and stationary objects through the obstacle 603.

Electro-magnetic radar signals 602 are produced by radar transmitters 601. The electromagnetic radar signals 602 travel through space, the intervening obstacle 603, reflect off of the target 604, and are recovered at radar receivers 605. Special beam-forming hardware and signal processing provides real-time images of the target 604 through the obstacle 603. The beam-forming hardware and signal processing is used to show real-time images of people through smoke, haze, rubble, avalanche debris, walls, and other obstacles. The obstacle penetrating dynamic radar imaging system 600 can aid first responders, such as police units responding to a hostage situation. In such a case, the officer holding the obstacle penetrating dynamic radar imaging system against a wall can see a moving picture of people located inside. Other uses include, but are not limited to, the following: concealed threat detection, hostage situations, facility protection, military and police action, search and rescue, prisoner monitoring, non-destructive evaluation, troop and soldier monitoring; prisoner monitoring, bridge inspection, medical imaging, medical diagnostics, and medical treatment.

The array control board 608 controls the firing of the delay board 606 and the programmable gain board 607. Each ACB can control up to 32 channels, where each channel can be either a time delay channel or a gain channel. As many ACBs as necessary can be used to control the elements in the array. In general, one channel is required for each transmitter element (time delay) and two channels for each receiver element (time delay and gain).

The obstacle penetrating dynamic radar imaging system 600 provides sweeping radar beams that provide an estimate of range to target. The radar transmitters 601 and radar receivers 605 can be small, low power ultra wideband radar units. The radar units can have the following features: dual channel radar; low-power; modular design; standardized (USB) interface; swept-range gating radar sensors; center frequency 2.4 GHz; bandwidth ~3 GHz; pulse repetition rate 4 MHz; pulse length ~12 ns; duty cycle ~20%; tuned antenna; high speed data transmitted from UWB radars to remote laptop or PDA; stem frame rate dependant on link data rate up to 1 Mbit/second; UWB radars sensitive to high-power radio frequency interference near their center frequency of ~1.9 GHz; data link is robust and capable of non-line-of-sight (LOS) communications over a distance of several hundred feet; and wireless communications.

The obstacle penetrating dynamic radar imaging system 600 uses return the radar signals to track motion. Signal and image processing algorithms are performed on a standard notebook computer, embedded DSP processor or similar device. A graphical user's interface for the operator will allow clear discrimination of targets in real-time as well as present a history of motion over past seconds. The detection, tracking, and imaging system will display dominant motion in a horizontal plane at the sensor height and motion history in real-time. The screen will be calibrated and display units of distance as well as processed radar signals will be seen as subplots.

The radar analog signals are digitized and used to triangulate and locate moving objects. The location estimate is then used to focus the radar to the location of the moving subject. A spectral estimation algorithm is then applied to provide detection and estimation of the human heartbeat and respiration signature (HRS) for that location. The radar antenna separation can be mechanically adjusted for a variety of angular resolutions. The field of view of the radar units comprises a radar lobe in the form of a plane parallel to the floor at or near the height of the radar antenna whose edges are determined by the antenna separation and field of view. A typical setting would provide coverage of an average sized room. Higher power systems can cover larger areas. All motion in the field of view is analyzed and therefore multiple people will produce multiple locations and HRS signatures. Estimates are updated fifteen times per second or faster. The information is displayed on a computer monitor screen or similar device. Display consists of an image representing motion in the room with icons or image highlighting to indicate locations of human subjects. Heartbeat and respiration rate estimates are also displayed for each location.

An azimuth estimate of a moving object can be calculated by signal and image filtering algorithms using multiple frame processing, non-stationary signal processing techniques, and triangulation using methods such as the Law of Cosines. This gives the ability to track a moving object precisely in space. Tracking the object allows focusing the range gate of a radar unit continuously to the moving target. This, in turn allows the continuous integration of localized spatial motion activity. Spectral estimation techniques are then used to estimate heartbeat and respiration rates.

The obstacle penetrating dynamic radar imaging system 600 can include a geo-location system for detection, tracking, and imaging of the individual or animal. Geo-location data for detected targets is provided by coupling known (radar location) position with target estimates for embodiments such as satellite-based and terrestrial radio frequency (RF) tracking applications. System can used in concert with existing geolocation systems such as satellite-based devices that use GPS or other means for geolocation via low-earth-orbit and geosynchronous satellites.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An obstacle penetrating dynamic radar imaging system for the detection, tracking, and imaging of an individual or animal located behind an obstruction, the radar imaging system utilizing an arbitrary set of points in space, comprising:
    more than five low power ultra wideband radar units that include transmitters and receivers, wherein said transmitters produce more than five sets of electro-magnetic signals that emanate from said units and travel through the obstruction to the individual or animal, and produce more than five sets of return radar signals from the individual or animal that travel back through the obstruction to said receivers, and
    a processing system for said more than five sets of return radar signals for detection, tracking, and imaging of the individual or animal, that includes
    an array control board,
    a timing and gain control circuitry that produces real-time video of 30 frames per second for detection, tracking, and imaging of the individual or animal,
    a delay control board,
    a gain control board,
    a transmitter delay control board,
    an analog to digital converter and amplifier gain board,
    an image construction board, and
    a video display monitor,
    wherein said delay control board, said gain control board, said transmitter delay control board, said analog to digital converter and amplifier gain board, and said image construction board calculate time delays and gains necessary to scan the arbitrary set of points in space and produce information, said information loaded onto said array control board which tells said gain control board and said analog to digital converter and amplifier gain board when to implement the necessary gains and produce a command,
    wherein said delay control board and said transmitter delay control board receive said command and delay said transmitters and receivers and said gain control board and said analog to digital converter and amplifier gain board apply appropriate gain to said return radar signals for compensation for attenuation through space, and
    wherein said return radar signals are transmitted to said video display monitor.

2. The obstacle penetrating dynamic radar imaging system of claim 1 wherein said more than five sets of low power ultra wideband radar units comprise radar transmitters, receivers, and antenna that produce more than five sets of sweeping radar beams.

3. The obstacle penetrating dynamic radar imaging system of claim 1 wherein said video display monitor is a touch-screen.

4. The obstacle penetrating dynamic radar imaging system of claim 3 wherein said processing system for said more than five sets of return radar signals includes a delay board, PGain board, array control board, and a computer.

5. The obstacle penetrating dynamic radar imaging system of claim 1 wherein the individual or animal is located behind an obstruction and including structure for positioning said more than five sets of low power ultra wideband radar units at fixed positions relative to said structure.

6. The obstacle penetrating dynamic radar imaging system of claim 1 wherein the individual or animal is located behind an obstruction and including a frame for positioning said more than five sets of low power ultra wideband radar units at fixed positions relative to said structure.

7. The obstacle penetrating dynamic radar imaging system of claim 1 wherein the individual or animal is located behind an obstruction and including a hand held shield for positioning said more than five sets of low power ultra wideband radar units at a fixed positions relative to said structure.

8. The obstacle penetrating dynamic radar imaging system of claim 1 including a geo-location system for detection, tracking, and imaging of the individual or animal.

9. An obstacle penetrating dynamic radar imaging system for the detection, tracking, and imaging of an individual or animal located behind an obstruction, the radar imaging system utilizing an arbitrary set of points in space, comprising:
    more than five low power ultra wideband radar means for producing more than five sets of return radar signals from the individual or animal that include transmitters and receivers, wherein said transmitters produce more than five sets of electromagnetic signals that emanate from said units and travel through the obstruction to the individual or animal, and produce more than five sets of return radar signals from the individual or animal that travel back through the obstruction to said receivers, and
    processing means for processing said more than five sets of return radar signals for detection, tracking, and imaging of the individual or animal to produce real-time video of 30 frames per second,
    said processing means including an array control board,
    timing and gain control circuitry that produces said real-time video of 30 frames per second,
    a delay control board,
    a gain control board,
    a transmitter delay control board,
    an analog to digital converter and amplifier gain board,
    an image construction board, and
    a video display monitor,
    wherein said delay control board, said gain control board, said transmitter delay control board, said analog to digital converter and amplifier gain board, and said image construction board calculate time delays and gains necessary to scan the arbitrary set of points in space and produce information, said information loaded onto said array control board which tells said gain control board and said analog to digital converter and amplifier gain board when to implement the necessary gains and produce a command,
    wherein said delay control board and said transmitter delay control board receive said command and delay said transmitters and receivers and said gain control board and said analog to digital converter and amplifier gain board apply appropriate gain to said return radar signals for compensation for attenuation through space, and wherein said return radar signals are transmitted to said video display monitor.

10. The obstacle penetrating dynamic radar imaging system of claim 9 wherein said means for producing more than five sets of return radar signals comprises more than five low power ultra wideband radar transmitters, receivers, and antenna that produce more than five sets of sweeping radar beams.

11. The obstacle penetrating dynamic radar imaging system of claim 9 wherein said video display monitor is a touch-screen.

12. The obstacle penetrating dynamic radar imaging system of claim 11 wherein said processing means for processing said more than five sets of return radar signals includes a delay board, PGain board, array control board, and a computer.

13. The obstacle penetrating dynamic radar imaging system of claim 9 wherein the individual or animal is located behind an obstruction and including structure for positioning said means for producing more than five sets of return radar signals at a fixed position relative to said structure.

14. The obstacle penetrating dynamic radar imaging system of claim 9 wherein the individual or animal is located behind an obstruction and including a frame for positioning said means for producing more than five sets of return radar signals at a fixed position relative to said structure.

15. The obstacle penetrating dynamic radar imaging system of claim 9 wherein the individual or animal is located behind an obstruction and including a hand held shield for positioning said means for producing more than five sets of return radar signals at a fixed position relative to said structure.

16. The obstacle penetrating dynamic radar imaging system of claim 9 including a geo-location system for detection, tracking, and imaging of the individual or animal.

17. A method of detecting and tracking an individual or animal wherein the individual or animal is located behind an obstruction and the radar imaging system utilizes an arbitrary set of points in space, comprising the steps of:

producing more than five sets of return radar signals from the individual or animal utilizing more than five low power ultra wideband radar units that include transmitters and receivers, wherein said transmitters produce more than five sets of electro-magnetic signals that emanate from said units and travel through the obstruction to the individual or animal, and produce more than five sets of return radar signals from the individual or animal that travel back through the obstruction to said receivers, processing said more than five sets of return radar signals for detecting and tracking of the individual or animal utilizing an array control board, timing and gain control circuitry, a delay control board, a gain control board, a transmitter delay control board, an analog to digital converter and amplifier gain board, an image construction board, and a video display monitor, and producing real-time video of 30 frames per second showing the individual or animal wherein said delay control board, said gain control board, said transmitter delay control board, said analog to digital converter and amplifier gain board, and said image construction board calculate time delays and gains necessary to scan the arbitrary set of points in space and produce information, said information loaded onto said array control board which tells said gain control board and said analog to digital converter and amplifier gain board when to implement the necessary gains and produce a command, wherein said delay control board and said transmitter delay control board receive said command and delay said transmitters and receivers and said gain control board and said analog to digital converter and amplifier gain board apply appropriate gain to said return radar signals for compensation for attenuation through space, and wherein said return radar signals are transmitted to said video display monitor.

18. The method of detecting and tracking an individual or animal of claim 17 wherein said step of processing said more than five sets of return radar signals comprises real time processing said more than five sets of return radar signals.

19. The method of detecting and tracking an individual or animal of claim 17 wherein said step of processing said more than five sets of return radar signals comprises real time processing said more than five sets of return radar signals at 30 frames/second.

20. The method of detecting and tracking an individual or animal of claim 17 wherein said step of producing more than five sets of return radar signals comprises using sweeping radar beams that provides an estimate of range to target.

21. The method of detecting and tracking an individual or animal of claim 17 wherein said step of producing more than five sets of return radar signals comprises using a steerable array of more than five microwave radars that enables up to 3 dimensional (3D) imaging to produce more than five sets of return radar signals from the individual or animal.

* * * * *